United States Patent [19]
Sinha et al.

[11] Patent Number: 5,606,130
[45] Date of Patent: Feb. 25, 1997

[54] METHOD FOR DETERMINING THE OCTANE RATING OF GASOLINE SAMPLES BY OBSERVING CORRESPONDING ACOUSTIC RESONANCES THEREIN

[75] Inventors: Dipen N. Sinha, Los Alamos, N.M.; Brian W. Anthony, Clearfield, Pa.

[73] Assignee: The Regents of the University of California, Los Alamos, N.M.

[21] Appl. No.: 218,012

[22] Filed: Mar. 25, 1994

[51] Int. Cl.$^6$ .................................................. G01N 9/24
[52] U.S. Cl. .................................................. 73/627; 73/599
[58] Field of Search .......................... 73/597, 599, 592, 73/620, 627, 646, 648

[56] References Cited

U.S. PATENT DOCUMENTS

| | | | |
|---|---|---|---|
| 5,062,296 | 11/1991 | Migliori | 73/579 |
| 5,152,180 | 10/1992 | Waldhauer, Jr. | 73/579 |
| 5,359,541 | 10/1994 | Pope et al. | 73/32 A |
| 5,408,863 | 4/1995 | Sawyers et al. | 73/35 |
| 5,408,880 | 4/1995 | Rhodes et al. | 73/597 |
| 5,426,977 | 6/1995 | Johnston et al. | 73/595 |

*Primary Examiner*—Richard Chilcot
*Assistant Examiner*—Max H. Noori
*Attorney, Agent, or Firm*—Samuel M. Freund

[57] ABSTRACT

A method for determining the octane rating of gasoline samples by observing corresponding acoustic resonances therein. A direct correlation between the octane rating of gasoline and the frequency of corresponding acoustic resonances therein has been experimentally observed. Therefore, the octane rating of a gasoline sample can be directly determined through speed of sound measurements instead of by the cumbersome process of quantifying the knocking quality of the gasoline. Various receptacle geometries and construction materials may be employed. Moreover, it is anticipated that the measurements can be performed on flowing samples in pipes, thereby rendering the present method useful in refineries and distilleries.

7 Claims, 3 Drawing Sheets

METHOD FOR DETERMINING THE OCTANE RATING OF GASOLINE SAMPLES BY OBSERVING CORRESPONDING ACOUSTIC RESONANCES THEREIN

The present invention relates generally to the measurement of octane ratings in samples of gasoline and, more particularly, to the observation of corresponding acoustic resonant frequencies in a sample thereof which may be related to the octane rating of the gasoline therein. This invention was made with Government support under Contract No. W-7405-ENG-36 awarded by the U.S. Department of Energy. The Government has certain rights in the invention.

BACKGROUND OF THE INVENTION

Various state and federal laws require that the octane ratings posted on gasoline pumps at gas stations are within certain limits of accuracy. Octane rating is a number indicating the degree of knocking of a fuel mixture under standard test conditions. To prevent the fuel-wasting, potentially damaging engine knock at all engine speeds and loads, gasoline must have high antiknock quality (octane number) throughout its entire distillation range.

Early in the study of knock, it was recognized that the chemical structure of fuel hydrocarbons largely determines their tendency to cause knock, and that straight-chain paraffins are more prone to knocking than branched-chain paraffins, olefins, or cyclic hydrocarbons. Soon after the discovery of antiknocking additive agents, it became evident that a yardstick was needed for measuring the antiknock quality of motor fuels. In 1926, Ethyl Corporation developed the octane scale, which has become the worldwide standard for that purpose. For the zero of the scale, a straight-chain hydrocarbon, n-heptane, is selected since it burns with considerable knock. For 100, a nonknocking branched-chain hydrocarbon 2,2,4-trimethylpentane (often incorrectly referred to as isooctane) is chosen. By blending these two hydrocarbons in varying percentages, a primary reference fuel can be produced to match the knock resistance of any gasoline sample. Octane number is defined as the percentage of isooctane required in a blend with n-heptane to match the knocking behavior of the gasoline being tested. Thus, if a blend of 87% 2,2,4-trimethylpentane and 13% n-heptane is required to match the knock resistance of a particular gasoline sample when both are run in a test engine under specified conditions, the sample is said to have an octane number of 87.

The CFR (Cooperative Fuel Research) knock-test engine has been adopted as the standard for determining octane number. Basically, it is a single-cylinder, four-stroke engine in which the compression ratio can be varied at will. Auxiliary equipment includes means for detecting pressure impulses from detonation, an electronic amplifier, and a meter to record knock intensity. To determine a fuel's antiknock quality, the CFR engine is operated on the fuel under a standard set of conditions and its compression ratio is adjusted to give a standard level of knock intensity. The method is cumbersome and time-consuming and the equipment is expensive. For frequent monitoring of gasoline octane rating at gas stations and at distillation plants, a simpler method is needed.

Accordingly, it is an object of the present invention to provide a method for determining the octane rating of samples of gasoline without requiring engine testing thereof.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for determining the octane rating of a gasoline sample includes the steps of establishing a pattern of acoustic interference peaks in the liquid sample to be investigated by applying a periodic acoustical signal having a chosen frequency to the outside of a receptacle containing the gasoline sample, or between two substantially parallel transducers within the gasoline; sweeping the frequency of the applied acoustical signal over a chosen frequency at the peak maximum range; and measuring the frequency of the interference peaks in the chosen frequency range.

It is preferred that the acoustical frequency range is chosen such that the difference in the interference patterns of gasoline samples having different octane ratings is maximized.

Benefits and advantages of the present invention include the ability to measure the octane rating in a gasoline sample without contacting the liquid itself. The method is suitable for continuous monitoring of petroleum products in distillation plants and refineries. It is rapid, taking but a few seconds, and has excellent resolution. The required apparatus is inexpensive and can be highly portable; namely, the size of a hand-held calculator.

BRIEF DESCRIPTION OF THE DRAWINGS

The accompanying drawings, which are incorporated in and form a part of the specification, illustrate two embodiments of the present invention and, together with the description, serve to explain the principles of the invention. In the drawings.

DETAILED DESCRIPTION OF THE INVENTION

Briefly, the present invention permits the measurement of certain characteristics of liquids which affect the speed of sound therein. For example, a direct correlation between the octane rating of gasoline and the speed of sound in a gasoline sample has been experimentally observed. Therefore, changes in the speed of sound can be utilized as a sensitive parameter for determining changes in composition and, in particular, the octane rating of a gasoline sample can be directly determined through speed of sound measurements instead of by the cumbersome process of quantifying the knocking quality of the gasoline. There are several ways in which acoustic interference patterns may be established in a gasoline sample. One particularly effective technique involves using readily available piezoelectric transducers attached to the outside surface of the usual container for the liquid. Various receptacle geometries may be employed, so long as both transducer elements are located on the same side of the vessel. One transducer is excited by a swept, continuous, periodic sine-wave or other similar waveform signal, while the other transducer picks up the vibrations that result from interferences within the liquid at certain fixed frequencies and which depend on the separation between the two transducers, the nature of the receptacle, and the speed of sound in the liquid. The interferences are detected as resonances and can be easily observed using commercially available electronics. The receptacle may be constructed of any material that is inert to gasoline. Sturdy, thin-walled materials such as metals, glass, ceramics, and plastics may be employed.

Figure 1:
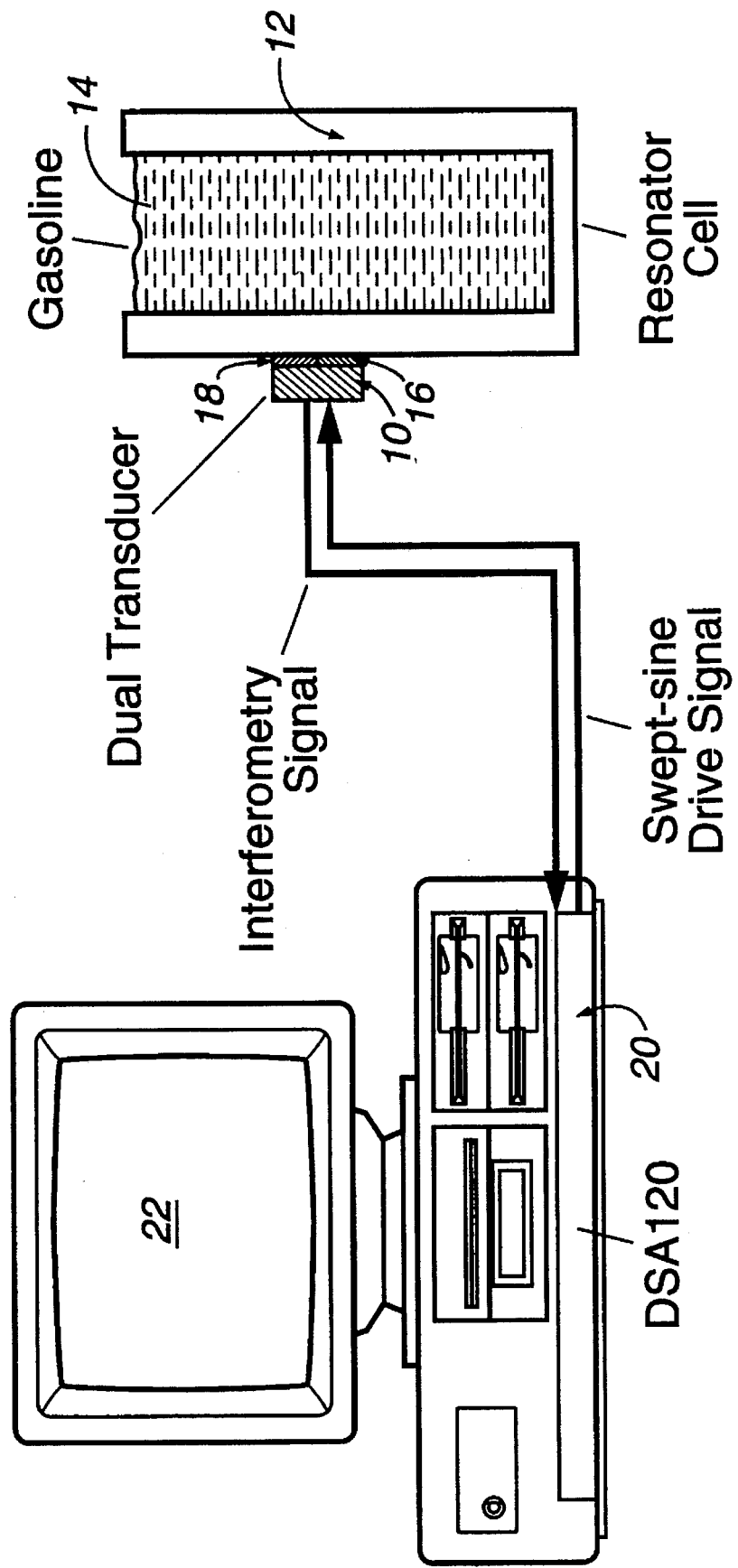
FIG. 1 is a schematic representation of the apparatus used to measure octane ratings of gasoline samples showing a dual transducer, apparatus for periodically driving one element of the dual transducer at acoustic frequencies, and apparatus for detecting and recording the acoustic vibrations established in the sample appearing on the second transducer element.

Reference will now be made in detail to the present preferred embodiments of the invention, examples of which are illustrated in the accompanying drawings. Similar or identical structure will be labeled with identical callouts. Turning now to FIG. 1, the two transducer apparatus utilized for impressing acoustical vibrations on the gasoline samples is illustrated. In this apparatus, the transducers do not make contact with the gasoline. Rather, transducer 10 is glued in contact with the outer surface of stainless steel receptacle 12, which contains the gasoline sample, 14, to be analyzed. Transducer 10 may either be a dual-element transducer, where two separate transducers 16, 18 are housed in a single enclosure (as shown in the Figure), but acoustically and electrically isolated, or two completely separated transducers located in the vicinity of one another on the same side of the sample vessel. The latter configuration somewhat distorts the interference peak shape, but does not affect the resonance frequencies.

A Panametrics Widescan Dual Transducer Model D744 was employed for the measurements. This transducer had a 2.25 kHz center frequency, and a 0.5 in.×0.5 in. element size. Although the two transducers are located in the same housing, they can be used simultaneously. Such transducers are generally used for high-resolution nondestructive testing of metal plates, etc. Other shapes, sizes and center frequency transducers may also be used; the model identified simply provides an example. However, it is important to select a crystal having its natural resonance frequency much higher than the cavity resonance frequency to which it is attached.

The receptacle wall thickness should be small (between 1–3 mm), but larger thicknesses also may be used. One of the transducer elements is used as a transmitter of acoustical energy to the receptacle, thereby establishing vibrational motion therein. The second transducer serves as the receiver.

Figure 2:
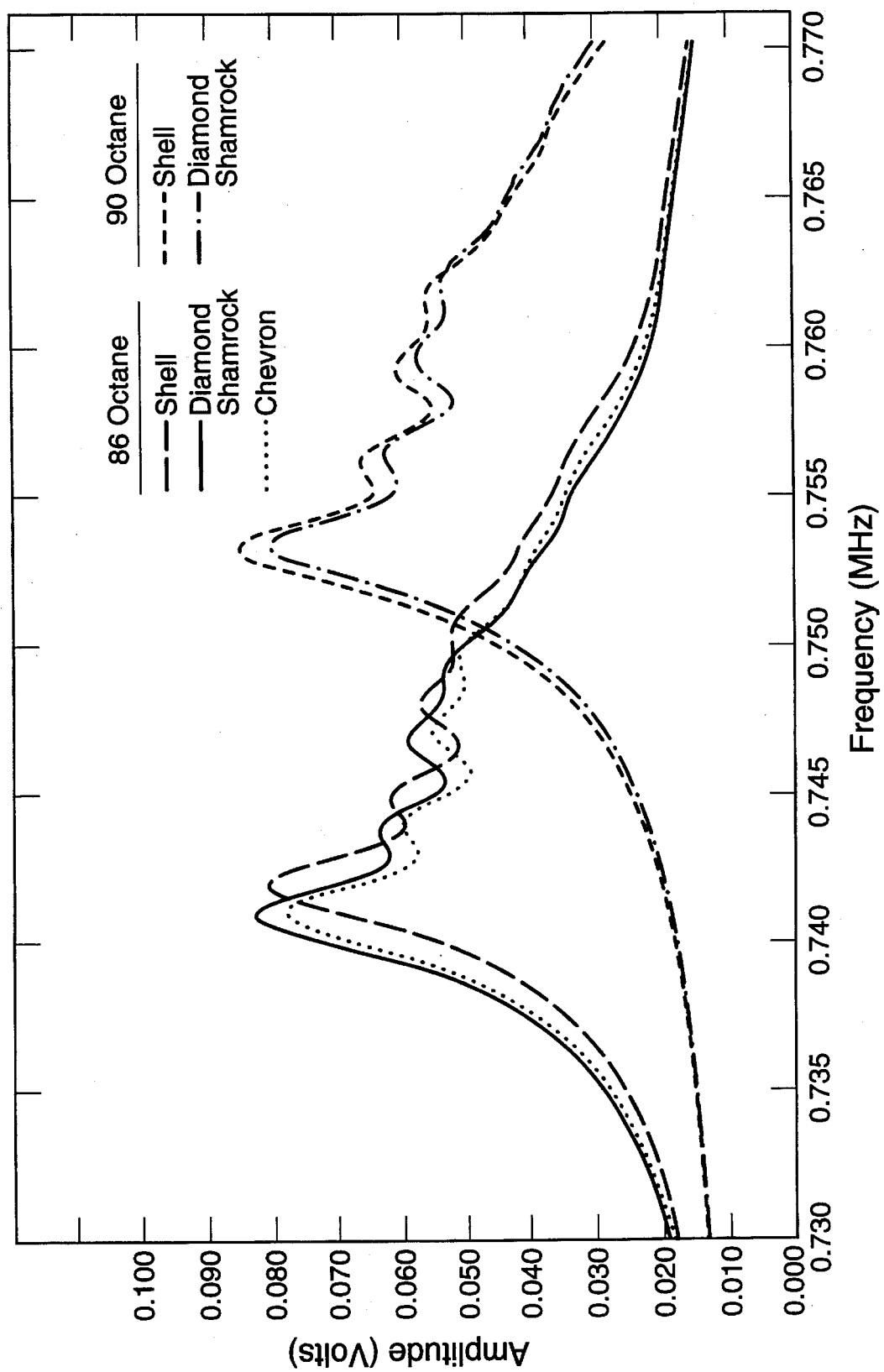
FIG. 2 shows the interference patterns generated, using the apparatus described in FIG. 1 hereof for several gasoline samples.

A Digital Synthesizer (DSA 120) and Analyzer PC Plug-in board (NEEL Electronics, Laguna Niguel, Calif.), 20, were employed both to drive the transmitter and to receive the interference signal from the receiver transducer. Any electronics system capable of providing a drive signal and detecting the amplitude of the received signal may be used for these measurements. The drive signal employed is a sine wave and is swept typically from a low frequency of 200 kHz to a high frequency of 1200 kHz. Computer 22, was used to control the synthesizer/analyzer, and to receive and process the data therefrom. Interference peaks, shown in FIG. 2, represent typical data obtained from several gasoline samples using the apparatus described in FIG. 1 hereof. The speed of sound in a liquid is proportional to the frequency difference between any two consecutive interference peaks for that particular liquid. If corresponding data from two different liquids (i.e., two different speeds of sound) are compared, there will be a good match between the two interference patterns at certain frequencies, but they will deviate from each other at other frequencies as shown in FIG. 2. This occurs since the two patterns have different periodicity. Consequently, to better resolve the data between two different liquids, it is important to select a frequency range where there is a large deviation in the pattern between two liquids. For example, the measurements on gasolines were restricted to the range between 730 and 770 kHz. The optimum frequency range depends on the particular geometry (the separation between the two opposing walls) of the resonator cell. The wall separation for the cell employed was about 1 cm. The volume of the gasoline sample used is not a factor in the measurement, so long as there is liquid covering the entire surface area of the inside of the vessel immediately in contact with the transducers.

Gasoline having widely separated and different octane levels was introduced into receptacle 12 for the demonstration of the present invention's use in determining the octane rating of gasolines. Gasoline from three different gas companies was employed to examine the sensitivity and repeatability of the invention. FIG. 2 shows the results of the measurements. The small secondary peaks associated with each central peak are due to lack of planarity between the walls of the cell. Only a single order interference peak is shown for clarity and resolution. The 86 octane gasolines from three different manufacturers are grouped together near 740 kHz whereas the 90 octane ones are close to 754 kHz. The difference between the two clusters of data is 14 kHz (14,000 Hz). The frequency step in the sweep frequency is 1 Hz. Thus, significant resolution in the data is possible. The shift in frequency between 86 and 90 octane gasoline is due to the change in speed of sound. The slight variation in the 86 octane data from different manufacturers is quite understandable, since existing octane measurement techniques do not provide better than 0.5 octane resolution, and so the gasoline from different manufacturers can vary slightly. Additionally, different manufacturers put small amounts of additives (e.g., detergents) in their gasoline, which will slightly affect the measurements.

Figure 3:
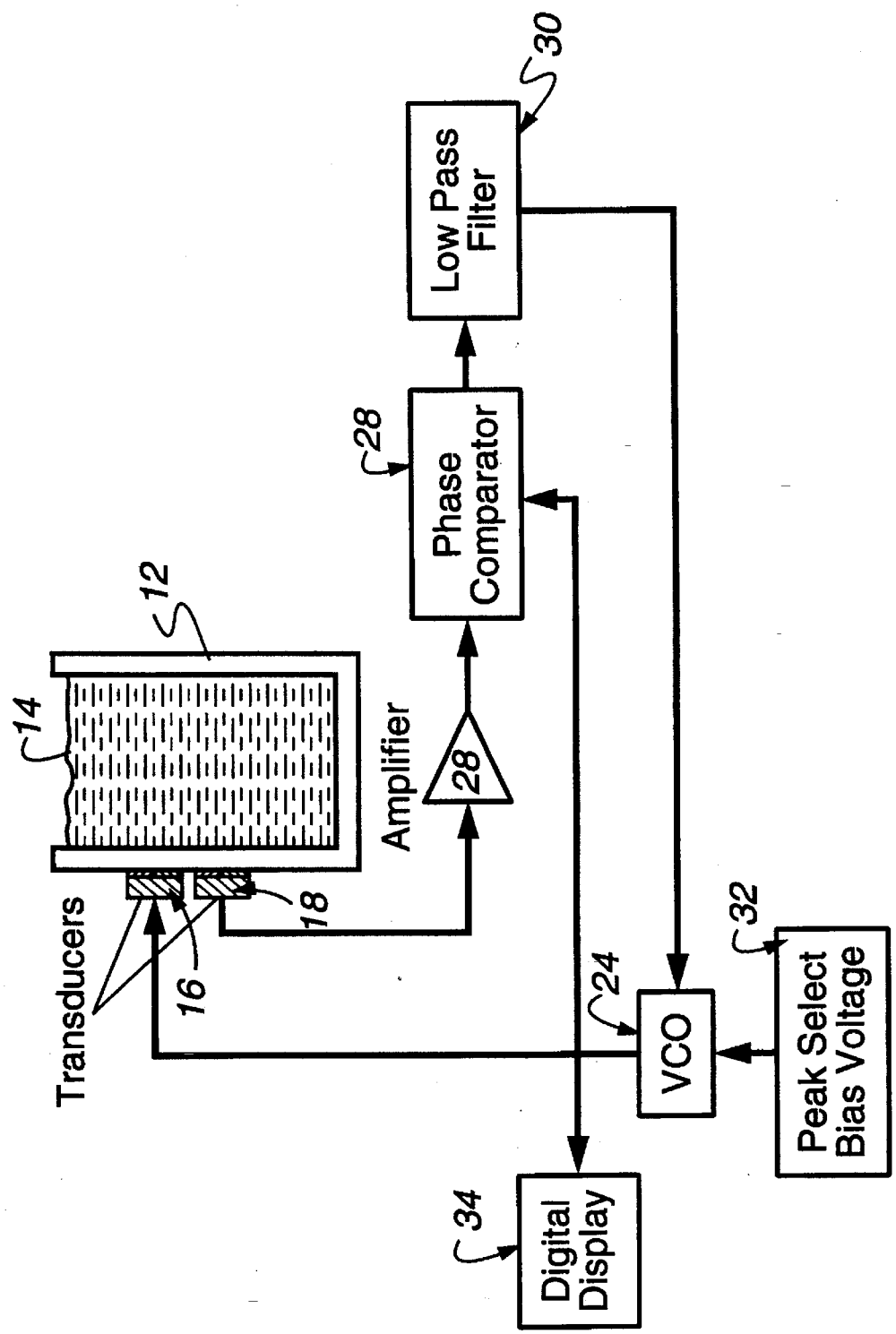
FIG. 3 is a schematic representation of a variation of the apparatus illustrated in FIG. 1 hereof, suitable for tracking the frequency shift of gasoline samples having different octane ratings.

Since the variation of gasoline octane manifests itself as a frequency shift in the interference peaks, one may obtain this information by automatically tracking the peak frequency of any particular order interference peak using feedback circuitry. The feedback circuit can be built using integrated circuit chips. A block diagram of a typical circuit useful for this purpose is presented in FIG. 3 hereof. This is a feedback circuit. Voltage-controlled oscillator 24 drives transducer 16 in the dual-transducer arrangement illustrated. The signal from receiving transducer 18 is first passed through amplifier 26 and then through phase-comparator 28 where it is compared with the output of oscillator 24. The output of phase comparator 28 is filtered through low-pass filter 30, and the resulting dc voltage is fed back to oscillator 24. Bias voltage supply 32 selects the frequency (particular interference peak) to be locked in. The feedback circuit then automatically maintains the lock and the result is displayed digitally in frequency counter 34, which may be calibrated directly in terms of the octane rating. The apparatus will not resonate when there is no liquid present inside receptacle 12. Once gasoline is introduced, however, the apparatus rapidly locks on to the frequency.

Other alternatives to this simple feedback circuit are possible. For example, one can introduce a please shifter (usually 90°) between oscillator 24 and the phase-comparator 28. This permits the apparatus to lock on the peak value of the particular interference peak. Since the principal interest lies in the frequency shift of the entire pattern, it is not critical that the lock is precisely at the peak position. Locking on the peak becomes critical, however, if a completely different liquid sample is to be analyzed which produces a large sound attenuation. Such liquids introduce changes in interference peak width in addition to the shift in frequency. However, for testing gasolines only of different octane rating, any error due to peak width variation is insignificant. The circuitry described in FIG. 3 hereof can be battery powered and can be packaged in a container the size of a hand-held calculator.

The foregoing description of the invention has been presented for purposes of illustration and description and is not intended to be exhaustive or to limit the invention to the precise form disclosed, and obviously many modifications and variations are possible in light of the above teaching. For example, it would be apparent to one having ordinary skill in the art of speed of sound measurements, after studying the subject disclosure, that one could utilize any method for measuring the speed of sound in liquids to observe the shift therein as a function of octane rating of the sample. Moreover, it would be apparent that one could also use cylindrical-shaped transducers designed to fit curved surfaces, such as pipes. Another alternative is to use a flat transducer and a shaped matching element designed to couple the flat surface of the transducer to the curved surface of the receptacle, although the sensitivity would be lower than that for a shaped transducer. Additionally, the liquid sample could be flowing through the receptacle, and the measurements would proceed essentially as described hereinabove, thereby making the present invention useful for controlling processes in oil refineries. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determining the octane rating of a sample of gasoline, said method comprising the steps of:

a. establishing a pattern of acoustic interference peaks in the gasoline sample to be investigated by applying a continuous periodic acoustical signal having a chosen frequency range; and b. measuring the frequency at the peak maximum of the interference peaks in the chosen frequency range.

2. The method as describe in claim 1, wherein the acoustical frequency range is chosen such that the difference in the interference patterns of gasoline samples having different octane ratings is maximized.

3. The method as described in claim 1, further including the step of comparing the frequency measured in said step of measuring the frequency with the corresponding frequency for a gasoline sample having a known octane rating.

4. The method as described in claim 1, wherein the step of establishing an acoustic interference pattern in the gasoline sample is accomplished by applying a continuous periodic acoustical signal having a chosen frequency to the outside of the receptacle containing the sample.

5. A method for comparing corresponding acoustical resonances in a sample of gasoline, said method comprising the steps of:

a. establishing a pattern of acoustic interference peaks in the gasoline sample to be investigated by applying a continuous periodic acoustical signal having a chosen frequency to the outside of the receptacle containing the sample;

b. sweeping the frequency of the applied signal over a chosen frequency range; and c. measuring the frequency at the peak maximum of the interference peaks in the chosen frequency range.

6. The method as describe in claim 5, wherein the acoustical frequency range is chosen such that the difference in the interference patterns of gasoline samples having different octane ratings is maximized.

7. The method as described in claim 5, further including the step of comparing the frequency measured in said step of measuring the frequency with the corresponding frequency for a gasoline sample having a known octane rating.

* * * * *